United States Patent
Klimberg et al.

(10) Patent No.: US 6,978,788 B2
(45) Date of Patent: Dec. 27, 2005

(54) MINIMALLY INVASIVE TREATMENT FOR BREAST CANCER

(75) Inventors: V. Suzanne Klimberg, Little Rock, AR (US); Steven Harms, Little Rock, AR (US); Soheila Korourian, Little Rock, AR (US)

(73) Assignee: The University of Arkansas for Medical Science, Little Rock, AR (US)

( * ) Notice: Subject to any disclaimer, the term of this patent is extended or adjusted under 35 U.S.C. 154(b) by 0 days.

(21) Appl. No.: 10/306,117

(22) Filed: Nov. 27, 2002

(65) Prior Publication Data

US 2003/0125640 A1    Jul. 3, 2003

Related U.S. Application Data

(60) Provisional application No. 60/337,626, filed on Dec. 10, 2001.

(51) Int. Cl.[7] .............................................. A61B 19/00
(52) U.S. Cl. .................................................... 128/898
(58) Field of Search ...................... 128/898; 600/562, 600/564; 604/19, 20, 22; 606/41

(56) References Cited

U.S. PATENT DOCUMENTS

| | | | |
|---|---|---|---|
| 5,590,655 A | 1/1997 | Hussman | 128/653.1 |
| 6,375,634 B1 * | 4/2002 | Carroll | 604/19 |
| 2002/0026188 A1 * | 2/2002 | Balbierz et al. | 606/41 |
| 2002/0052545 A1 | 5/2002 | Klimberg | 600/410 |

OTHER PUBLICATIONS

McManus et al., Advantages of outpatient breast surgery, Dec. 1994, American Surgeon, 60 (12) abstract provided.*

* cited by examiner

Primary Examiner—Corrine McDermott
Assistant Examiner—William H Matthews
(74) Attorney, Agent, or Firm—Benjamin Aaron Adler

(57) ABSTRACT

The present invention provides a minimally invasive, comprehensive same-day diagnosis and treatment method to remove tumor and ablate margins in breast cancer patients, comprising disease diagnosis by MRI and touch preparation cytology, followed by tumor removal and ablation of tumor margins.

2 Claims, 1 Drawing Sheet

MINIMALLY INVASIVE TREATMENT FOR BREAST CANCER

CROSS-REFERENCE TO RELATED APPLICATION

This non-provisional patent application claims benefit of provisional patent application U.S. Ser. No. 60/337,626, filed Dec. 10, 2001, now abandoned.

BACKGROUND OF THE INVENTION

1. Field of the Invention

The present invention relates generally to the field of cancer treatment. More specifically, the present invention relates to a method of same day diagnosis and treatment for cancer such as breast cancer.

2. Description of the Related Art

One in nine American women will develop breast cancer in their lifetime. It is the leading cause of cancer deaths in women 40–55 years of age and the second leading cause of cancer deaths in women overall. Breast cancer will be diagnosed in approximately one in eight women in their lifetime, and one in 30 will die of this disease. Breast cancer does occur in males but is much less common. Biopsy requests stem from a screening process generally performed via a physical examination (palpable) and/or mammogram (non-palpable). A biopsy is indicated if suspicious tissue is detected. Five out of six biopsies performed return benign indications.

It is desirable and often necessary to perform procedures of detecting, sampling, and testing lesions and other abnormalities in the tissues of humans and other animals for pre-malignant condition. This is particularly important in the diagnosis and treatment of patients with cancerous tumors. Typically, in the case of cancer, when a physician establish by means of known procedures (i.e. palpation, x-ray, MRI, or ultrasound imaging) that suspicious circumstances exist, a biopsy is performed to determine whether the cells are cancerous.

Biopsy may be an open or percutaneous technique. Open biopsy removes the entire mass (excisional biopsy) or a part of the mass (incisional biopsy). Percutaneous biopsy on the other hand is usually done with a needle-like instrument and may be either a fine needle aspiration (FNA) or a core biopsy. In fine needle aspiration biopsy, very small needles are used to obtain individual cells or clusters of cells for cytologic examination. The cells may be prepared such as in a Papanicolaou (Pap) smear. In core biopsy, as the term suggests, a core or fragment of tissue is obtained for histologic examination, which may be done via a frozen section or paraffin section. The chief difference between fine needle aspiration and core biopsy is the size of the actual tissue core taken. An imaging system having spectroscopic capabilities, such as the stereotactic guidance system described in U.S. Pat. No. 5,240,011 is employed to guide the extraction instrument to the lesion.

Depending on the procedure being performed, the suspicious lesion may be partially or completely removed. Visibility of the lesion by the imaging system may be hampered because of the distortion created by the extraction process itself as well as associated bleeding in the surrounding tissues. Although the lesion is removed and all fluids are continuously aspirated from the extraction site, it is likely that the process will "cloud" the lesion, thus impairing exact recognition of its margins. This makes it difficult to ensure that the entire lesion will be removed.

Often, the lesion is merely a calcification derived from dead abnormal tissue which may be cancerous or precancerous, and it is desirable to remove only a sample of the lesion rather than the entire lesion. This is because such a lesion actually serves to mark or define the location of adjacent abnormal tissue, so the physician does not wish to remove the entire lesion and thereby lose a critical means for later relocating the affected tissue. One of the benefits to the patient from core biopsy is that the mass of the tissue taken is small. However, oftentimes, either inadvertently or because the lesion is too small, the entire lesion is removed for evaluation, even though it is desirable to remove only a portion. Thus, if subsequent analysis indicates the tissue to be malignant, it is difficult for the physician to determine the precise location of the lesion in order to perform necessary additional procedures on adjacent potentially cancerous tissue. Malignant tissue requires removal, days or weeks later, of tissue around the immediate site of the original biopsy. Additionally, even if the lesion is found to be benign, there will be no evidence of its location during future examinations to mark the location of the previously removed calcification so that the affected tissue may be carefully monitored for future reoccurrence.

A number of procedures and devices for marking and locating particular tissue locations are known in the prior art. For example, location wire guides, such as that described in U.S. Pat. No. 5,221,269 are well known for locating lesions, particularly in the breast. The device comprises a tubular introducer needle and an attached wire guide which has at its distal end a helical coil configuration for locking into position about the targeted lesion. The needle is introduced onto the breast and guided to the lesion site using an imaging system of a known type, for example, x-ray, ultrasound or magnetic resonance imaging (MRI), at which time the helical coil at the distal end is deployed about the lesion. The needle may then be removed from the wire guide which remains in a locked position distally about the lesion for guiding a surgeon down the wire to the lesion site during subsequent surgery. While such a location system is effective, it is obviously intended and designed to be only temporary, and is removed once the surgery or other procedure has been completed.

Other devices are known for marking external regions of a patient's skin. For example, U.S. Pat. No. 5,192,270 to Carswell, Jr. discloses a syringe which dispenses a colorant to give a visual indication on the surface of the point at which an injection has or will be given. Similarly, U.S. Pat. No. 5,147,307 to Gluck discloses a device which has patterning elements for impressing a temporary mark in a patients skin for guiding the location of an injection or the like. It is also known to tape or otherwise adhere a small metallic marker, e.g. a 3 millimeter diameter lead sphere, on the skin of a human breast in order to delineate the location of skin calcifications. Obviously, however, none of these approaches are useful for marking and delineating internal tissue abnormalities, such as lesions or tumors.

A method of identifying and treating abnormal neoplastic tissue or pathogens within the body is described in U.S. Pat. No. 4,649,151 to Doughety et al. In this method, a tumor-selective photosensitizing drug is introduced into a patient's body, where it is cleared from normal tissue faster than it is cleared from abnormal tissue. After the drug clears normal tissue but before it has cleared abnormal neoplastic tissue, the abnormal neoplastic tissue may be located by the luminescence of the drug within the abnormal tissue. The fluorescence may be observed with low intensity light, some of which is within the drug's absorbency spectrum. Once detected, the tissue may be destroyed by further application of higher intensity light having a frequency within the absorbency spectrum of the drug. Of course, this method also is only a temporary means for marking the abnormal tissue. Additionally, once the abnormal tissue has been destroyed during treatment, the marker is destroyed as well.

It is also known to employ biocompatible dyes or stains to mark breast lesions. First, a syringe containing the colorant is guided to a detected lesion by an imaging system. Later, during the extraction procedure, the surgeon harvests a tissue sample from the stained tissue. However, while such staining techniques can be effective, it is difficult to precisely localize the stain. Also, the stains are difficult to detect flouoroscopically and may not always be permanent.

Thus, the prior art is deficient in a treatment system for breast cancer that remove the tumor and ablate the margin of the tumor. The present invention fulfills this long-standing need and desire in the art.

SUMMARY OF THE INVENTION

Recent trends in breast cancer treatment favor breast conservation surgery, with an emphasis on improved cosmetic results. However, prior to surgery, the patients must wait for pathology results of a biopsy before a final diagnosis can be given. Further waiting is required before the patients can be treated for removal of a malignant lesion. Moreover, breast conservation surgery via lumpectomy often results in some deformity and requires repeated surgery to establish a clear margin around the malignant lesion.

The present invention provides a minimally invasive, comprehensive same-day diagnosis and treatment system for patients with small ($\leq 1.5$ cm in diameter) breast lesions. The system provides improved cosmetic results, reduced recovery time and requires less waiting time for diagnosis and treatment. The treatment method uses imaging techniques such as MRI or ultrasound to predict the extent of the disease and guide the removal of the tumor. The procedure further uses touch preparation cytology for diagnosis and any known ablation techniques for the establishment of margins.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention as well as others which will become clear are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

DETAILED DESCRIPTION OF THE INVENTION

Figure 1:
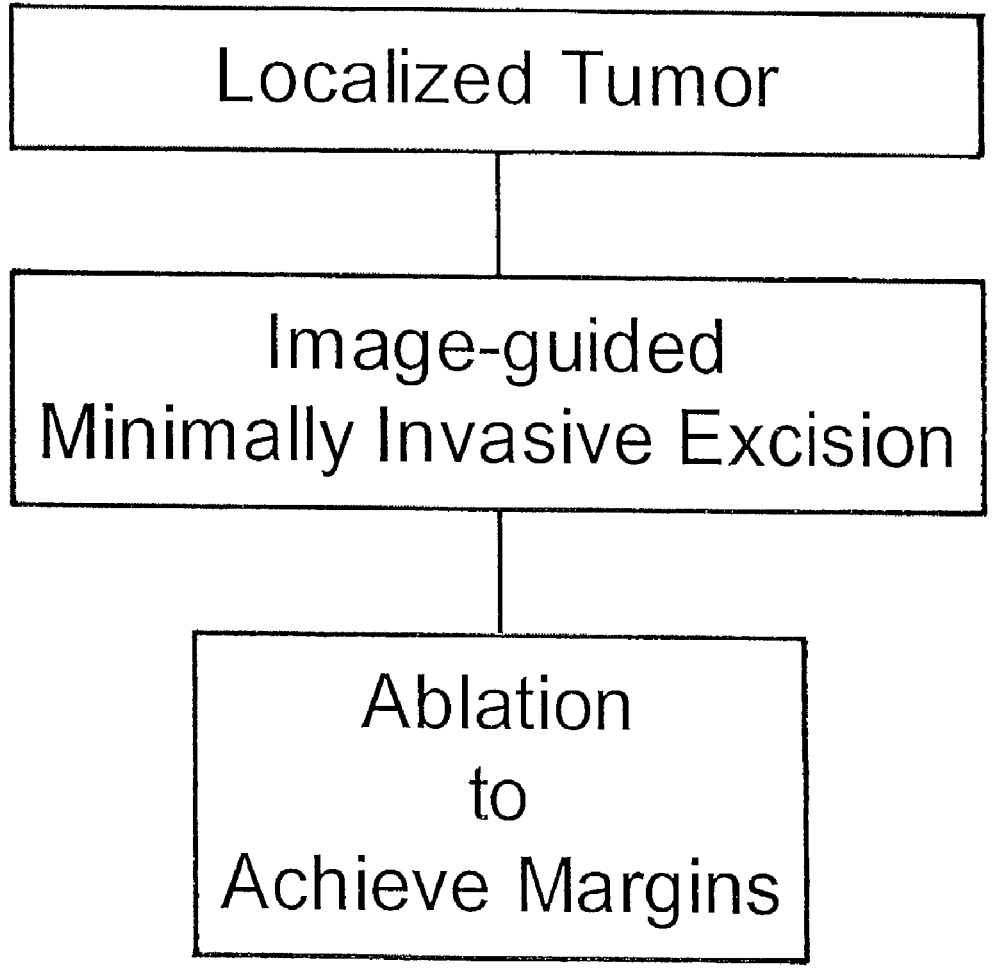
FIG. 1 shows a schema for the minimally invasive, comprehensive same-day diagnosis and treatment method for breast cancer.

The present invention is directed to a comprehensive same-day diagnosis and treatment system for patients with small ($\leq 1.5$ cm in diameter) breast lesions. An object of the present invention is not to simply ablate tumor but to ablate margins as well.

In one embodiment of the present invention, the treatment method uses the Mammotome® Breast Biopsy System to remove abnormal tissue. Other percutaneous devices known to one of skill in the art can also be used. Imaging systems such as MRI or ultrasound are used to predict the extent of the disease, guide the removal of the tumor and document ablation zone, whereas diagnosis is provided by touch preparation cytology.

The Mammotome® Breast Biopsy System is a minimally invasive, image guided procedure (stereotactic or ultrasound) that helps physicians locate breast abnormalities and obtain tissue samples for diagnosis. In stereotactic procedures, the patient lies face down on a special table with the breast protruding through a hole in the table. The breast is lightly compressed to immobilize it. This table is also a mammogram table that allows the physician to get a clear mammographic image of the area to be sampled. The table is connected to a computer that processes digital images. Placement of the sampling device is guided by a computerized system using x-rays.

The Mammotome® Breast Biopsy System procedure can be performed through a ⅛" skin incision in less than one hour under a local anesthetic. The Mammotome® is capable of sampling a variety of breast abnormalities, such as microcalcifications, asymmetric densities, solid masses or nodules. It can obtain multiple tissue samples with one insertion, whereas other methods require multiple insertions. When the biopsy is completed, the tissue samples are sent to a laboratory for pathologic analysis. A procedure which requires no sutures, the Mammotome® is a valuable tool that helps physicians accurately diagnose breast cancer in its earliest stages.

The Mammotome® Breast Biopsy System is a well-established diagnostic tool that allows more accurate diagnosis and permits removal of larger specimens than is possible with core biopsy. Core needle biopsy limits the amount of tissue available to pathologists for establishing the histologic diagnosis and biochemical markers. A core biopsy may show ductal carcinoma in situ, but the final pathology of the lumpectomy specimen may demonstrate focal areas of infiltrating carcinoma. In contrast, the Mammotome® System uses single-insertion technology with vacuum assistance for removal of an imaged abnormality via a sutureless incision. The present invention uses the Mammotome® System as a treatment tool to remove small lesions ($\leq 1.5$ cm in diameter) followed by tissue ablation to establish margins. Other percutaneous devices known to one of skill in the art can also be used, and this treatment paradigm is potentially more accurate than surgery.

In order to provide same-day treatment to patients, pre-procedure fine needle cytology or intra-procedure touch preparation cytology can be used for immediate diagnosis of lesions. The touch-prep method, which involves touching the specimen to a glass slide to which tumor cells will adhere, allows simple, quick (2–3 minutes), safe (no loss of diagnostic material), and accurate diagnosis at the time of surgery.

Imaging techniques such as MRI can be used as the imaging modality for the present invention. MRI of the breast using the RoDEO (Rotating Delivery of Excitation Off-resonance) pulse sequence has recently been developed to diagnose and determine the extent of local breast cancer. Validation studies comparing breast Rotating Delivery of Excitation Off-resonance MRI to serially sectioned mastectomy specimens showed a high degree of correlation in the ability of Rotating Delivery of Excitation Off-resonance MRI to predict disease extent and lesion margins.

The present invention can employ a number of ablation techniques known to one skilled in the art. For example, clinical and basic science studies have shown that interstitial laser photocoagulation (ILP) can effectively ablate cancers via a percutaneous approach. Preliminary results of MRI-directed interstitial laser photocoagulation in 30 patients with breast cancer indicated that the procedure was well-tolerated and side effects were similar to those of routine stereotaxic needle biopsy. Each patient has between one and five ablation zones for a total of 68 treatment zones. When the entire 10-minute treatment session was completed, the pathology correlation determined effective cell death in all cases. The histologic determination of treatment zones by proliferating cell nuclear antigen (PCNA) staining within the tumor matched the MRI estimates of zone size in all cases. Besides interstitial laser photocoagulation, ablation of tumor tissue can be accomplished by cryotherapy, radiofrequency, or ultracision with the harmonic scapel.

Major benefits of the same-day treatment system disclosed herein include improved cosmetic result, reduced recovery time, and less stress for the patient as no waiting for a diagnosis or treatment decision is involved. In addition, a same-day diagnosis and treatment system also means lowered cost due to reduced hospital or same-day surgery time. Moreover, one of skill in the art would recognize that the treatment method disclosed herein is also applicable to other cancers besides breast cancer.

In one embodiment of the present invention, there is provided a minimally invasive method for diagnosing, removing and ablating margins of a tumor in a breast of an individual as a same day treatment, comprising the steps of imaging the breast of the individual to locate a potential tumor or to determine the extent of an existing tumor within the breast or a combination thereof; obtaining a cell specimen from the tumor pre-procedure or intra-procedure; preparing cytology samples from the specimen for diagnosis; excising the tumor from the breast under imaging guidance; and ablating the tumor margins in the breast where performing the method steps on the same day results in a minimally invasive treatment of the individual.

In all aspects of this embodiment the breast is imaged by MRI. The cytology samples may be prepared by touch preparation cytology or fine needle cytology. The excision of the tumor is directed by ultrasound or MRI and the ablation of the tumor margin is by interstitial laser photocoagulation, cryotherapy, radiofrequency, or ultracision with a harmonic scalpel. A representative example of a breast tumor is one having a diameter of about 1.5 cm or less.

One skilled in the art will appreciate readily that the present invention is well adapted to carry out the objects and obtain the ends and advantages mentioned, as well as those objects, ends and advantages inherent herein. The methods and procedures described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A minimally invasive, same day treatment method for diagnosing and removing a small tumor in a breast of an individual, comprising:

locating a small tumor of about 1.5 cm diameter or less within the breast via MRI imaging thereof;

excising the small tumor from the breast under MRI guidance via a single, sutureless percutaneous excision;

diagnosing the excised small tumor as cancerous immediately from touch preparation cytology of a sample therefrom; and ablating a tumor margin around the edge of the excisional site in the breast after excising and diagnosing the tumor;

wherein percutaneously excising the small tumor with a single sutureless incision followed by ablating a margin around the excisional site are minimally invasive to the individual in combination with immediately diagnosing the small tumor provides a minimally invasive, same day treatment method for removing said small tumor from a breast of the individual.

2. The method of claim 1, wherein ablating the tumor margin is by a method selected from the group consisting of interstitial laser photocoagulation, cryotherapy, radiofrequency, and ultracision with a harmonic scalpel.

* * * * *